United States Patent [19]

Ramey et al.

[11] 4,448,969

[45] May 15, 1984

[54] CYCLIC ETHER OR CARBONATE ALKYLATION PRODUCTS OF 2,2,5,5-TETRAMETHYLIMIDAZOLIDIN-4-ONE AND DERIVATIVES, THEIR PREPARATION, AND THEIR USE AS STABILIZERS FOR SYNTHETIC POLYMERS

[75] Inventors: Chester E. Ramey; Charles J. Rostek, Jr., both of Chagrin Falls, Ohio

[73] Assignee: Ferro Corporation, Cleveland, Ohio

[21] Appl. No.: 371,201

[22] Filed: Apr. 23, 1982

[51] Int. Cl.$^3$ ............................................ C07D 233/00
[52] U.S. Cl. .................................................. 548/301
[58] Field of Search ...................... 524/106, 324, 101; 548/337, 341, 301

[56] References Cited

U.S. PATENT DOCUMENTS 3,971,757  7/1976  Rasberger ........................... 524/106
4,207,229  6/1980  Spivack ............................... 524/101

*Primary Examiner*—John Kight, III
*Assistant Examiner*—Kriellion Morgan
*Attorney, Agent, or Firm*—Robbins & Laramie

[57] ABSTRACT

Amide or 3-alkylation of 2,2,5,5-tetra-substituted imidazolidin-4-ones, using either monofunctional or polyfunctional cyclic ethers as alkylating agents, under basic conditions, or an ethylene carbonate. The cyclic ether reactants may be aldehydes or ketones having a single carbon atom in the ring. The alcohols obtained from ether addition to the 2,2,5,5-tetrasubstituted imidazolidin-4-ones may be converted to esterified derivatives by treatment with carboxylic acids or esters. Representative esters from mono- or polyalkylated imidazolidinones possess superior light stabilizing activity. Also embraces new compounds that are useful as light stabilizers for synthetic polymers.

2 Claims, No Drawings

CYCLIC ETHER OR CARBONATE ALKYLATION PRODUCTS OF 2,2,5,5-TETRAMETHYLIMIDAZOLIDIN-4-ONE AND DERIVATIVES, THEIR PREPARATION, AND THEIR USE AS STABILIZERS FOR SYNTHETIC POLYMERS

BACKGROUND OF THE INVENTION

1. Field of the Invention

This invention relates to the stabilization of organic polymers against the harmful degradative effects, such as discoloration and embrittlement, caused by exposure to ultraviolet light. More specifically, this invention relates to new derivatives of 2,2,5,5-tetramethylimidazolidin-4-one, a process for their manufacture, their use as light stabilizers for organic polymers, and the polymers stabilized with these additives.

2. Description of the Prior Art

It has been proposed to stabilize polymeric materials against ultraviolet light deterioration by the use of various types of ultraviolet absorbers. Thus, U.S. Pat. No. 3,004,896 discloses for this purpose 2(2-hydroxyphenyl) benzotriazole derivatives, while U.S. Pat. No. 3,189,630 discloses certain metal salts of hydroxybenzoic acids which are useful as actinic stabilizers in synthetic polymers.

Additionally, derivatives of 2,2,5,5-tetramethylimidazolidin-4-one have been disclosed as ultraviolet light stabilizers in the following: U.S. Pat. Nos. 3,532,703, 3,645,965, 3,971,757, and 3,956,310; Neth. Appln. 74-08217; Swiss Pat. No. 579,117; French Pat. Nos. 1,528,233 and 2,234,294; Danish Pat. No. 3365/74; British Pat. No. 1,453,099; German Offens. 1,817,703 and 2,500,313; and Japanese Kokais 76-26,874 and 77-27,458.

The Murayama et al. patent, 3,532,703, for example, relates to imidazolidine-N-oxides having the formula

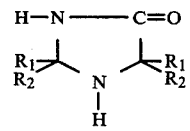

wherein $R_1$ and $R_2$, which may be the same or different, represent an alkyl group or they may be linked together with the carbon atom to which they are attached to form a saturated 5- or 6-membered homocyclic ring which may be substituted with an alkyl group or a group of the formula

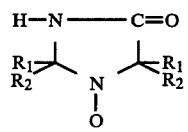

wherein $R_1'$ and $R_2'$, which may be the same or different, each represent an alkyl group or they may be linked together with the carbon atom to which they are attached to form a saturated 5- or 6-membered homocyclic ring which may be substituted with an alkyl group. These compounds are produced by treating an imidazolidine derivative having the formula

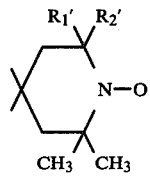

wherein $R_1$ and $R_2$ are as defined above, with a peroxide. These imidazolidine-N-oxides of Murayama et al. are said to exert a stabilizing effect on polyolefins against photodeterioration. This patent corresponds to French Pat. No. 1,528,233.

A later Murayama et al. patent, 3,645,965, discloses 2,5-tri- and 2,5-tetra-substituted-4-oxo-imidazolidine compounds having the formula

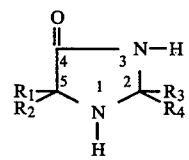

wherein the several R substituents may be many different organic radicals. A few specific representative compounds disclosed include:

2,2,5,5-tetramethyl-4-oxoimidazolidine (M.P. 169°–170° C.);

2,5-dimethyl-2,5-diethyl-4-oxoimidazolidine (M.P. 77°–79° C.);

2,5,5-trimethyl-2-isobutyl-4-oxoimidazolidine (M.P. 126°–128° C.);

2,5-dimethyl-2,5-diisobutyl-4-oxoimidazolidine;

1,4-diaza-2,2-dimethyl-3-oxo-spiro[4.5]decane (M.P. 193°–194° C.); and cyclohexane-1-spiro-2'-(4'oxoimidazolidine)-5'-spiro-1"-cyclohexane (M.P. 219°–220° C.).

This patent corresponds in part to German Offen. 1,817,703.

The Rasberger patent, 3,971,757, discloses a host of compounds including, for example, some alkylation products of 2,2,5,5-tetramethylimidazolidin-4-one and ethylene oxide, e.g.

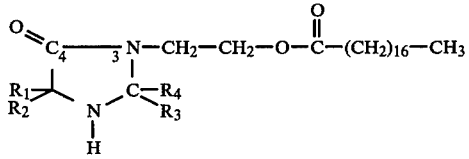

wherein $R_1$, $R_2$, $R_3$ and $R_4$ independently of one another each denote an alkyl group or $R_1$ and $R_2$ and/or $R_3$ and $R_4$ together with the C atom to which they are bonded form a cycloalkyl radical. Rasberger also discloses related derivatives where the substitutent at the 3-N may be, for example, $-CH_2CH_2OH$; $-CH_2CHOH-CH_3$; $-CH_2CH_2OOCCH_3$; $-CH_2CH_2OOCC_7H_{15}$; $-CH_2CH_2OOCC_{11}H_{23}$; $-CH_2CH_2OOCC_{17}H_{35}$;

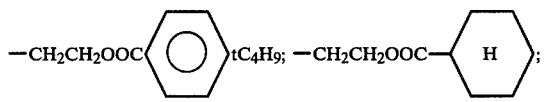

—$CH_2OC_4H_9$; —$CH_2CH_2OC_8H_{17}$, and many others. U.S. Pat. No. 3,971,757 is believed to be an equivalent of Neth. Appln. 74-08217.

In U.S. Pat. No. 3,956,310, believed to be equivalent to Ger. Offen. 2,500,313, many N-carbamoyl imidazolidinones are described. In one preferred embodiment, the compounds have the formula

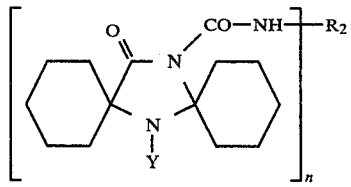

where n may be 1 or 2; Y is 0, H, or either a straight or a branched-chain lower alkyl residue, and when n is 1, $R_2$ is a straight or branched chain alkyl residue having from 1 to 20 carbon atoms, a straight or branched chain alkenyl residue having from 3 to 18 carbon atoms, a substituted or unsubstituted cycloalkyl residue having from 5 to 14 carbon atoms, a substituted or unsubstituted aryl residue having from 6 to 10 carbon atoms, or an aralkyl residue having from 7 to 18 carbon atoms; and when n is 2, $R_2$ is a straight or branched alkylene residue having from 2 to 20 carbon atoms, a substituted or unsubstituted arylene residue having from 6 to 10 carbon atoms or an aralkylene residue having from 7 to 18 carbon atoms. Suitable substituents on $R_2$ cycloalkyl or aryl residues are halogen atoms or alkyl groups having from 1 to 12 carbon atoms or alkoxy groups having from 1 to 4 carbon atoms.

French Pat. No. 2,234,294, which appears to correspond to British Pat. No. 1,453,099, and to Swiss Pat. No. 579,117, discloses compounds corresponding to the general formula:

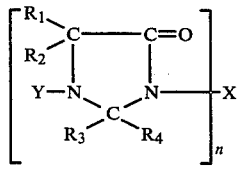

wherein $R_1$, $R_2$, $R_3$ and $R_4$ each represent, independently of each other, an alkyl radical, or each of $R_1$ and $R_2$, and $R_3$ and $R_4$, may form, together with the ring carbon to which they are bonded, a 5 to 7 carbon cycloalkyl;

Y is H or O;

n is an integer of 1 to 4, and

X may be any one of several different substituents, depending in part on the value of n. Thus, when n is 1, X may be alkyl.

Japanese Kokai 76-26,874 discloses imidazolidyl propionitriles of the general formula

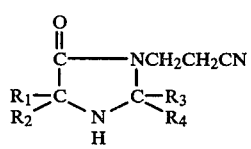

where $R_1$, $R_2$, $R_3$ and $R_4$ are hydrocarbon groups and can be the same or different, and $R_1$ and $R_2$, and/or $R_3$ and $R_4$, together with the ring carbon to which they are attached respectively, may form a cycloalkyl group.

Japanese Kokai 77-27,458 describes stabilizers for polyurethanes of the formula

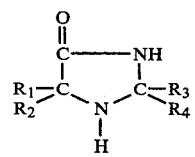

where $R_1$, $R_2$, $R_3$ and $R_4$ have the same meanings as in Japanese Kokai 76-26,874, but may also form heterocyclic groups.

BRIEF SUMMARY OF THE INVENTION

This invention achieves amide or 3-alkylation of 2,2,5,5-tetra-substituted imidazolidin-4-ones using either monofunctional or polyfunctional cyclic ethers as alkylating agents, under basic conditions, or ethylene carbonate.

The cyclic ether reactants used as alkylating agents may be aldehydes or ketones having a single carbon atom in the ring. The resulting alcohols obtained from single or multiple ether addition to the 2,2,5,5-tetrasubstituted imidazolidin-4-ones may be converted to fully esterified derivatives by treatment with carboxylic acids or esters.

The representative esters from mono- or polyalkylated imidazolidinones possess superior light stabilizing activity. This superior activity is a property of imidazolidinone derivatives which are substituted in the amine or 1-position by either an alkyl group (which may be substituted, as described below) or a hydrogen atom.

The present invention also embraces new compounds that are useful as light stabilizers for synthetic polymers and that correspond generally to the formula

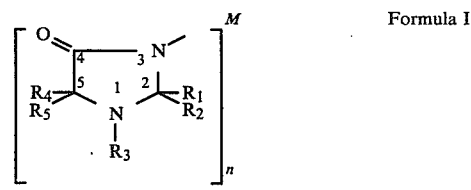

Formula I wherein:

$R_1$, $R_2$, $R_4$ and $R_5$ independently of one another each denote an alkyl group having 1 to 6 carbons, and in addition, $R_1$ and $R_2$ and/or $R_4$ and $R_5$, together with the ring carbon to which they are bonded respectively, may form a cycloalkyl ring having a total per ring of 5 or 6 carbons;

$R_3$ denotes: hydrogen; the oxyl radical —O; alkyl having 1 to 6 carbons; oxyalkyl having up to 6 carbons; oxyalkyl-derived substituents including hydroxyalkyl having 2 or 3 carbons, and hydroxyalkyl having 2 to 3 carbons wherein the following substituent(s) may be on the carbon beta to N:

an oxirane group that includes the beta carbon and replaces the hydroxyl group;

alkyl of up to 4 carbons, where the hydroxyl group remains on the beta carbon, or is replaced by

and
an ester group,

where $R_7$ is selected from the group consisting of an alkyl group having up to 20 carbon atoms, an alkyl alkoxycarbonyl group of an aliphatic monobasic or dibasic acid having from 2 to 20 carbons, and the group:

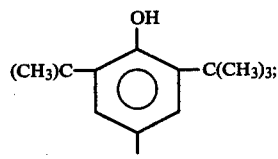

and, if n is 2, then M is selected from the group consisting of

where $R_{10}$ may be H,

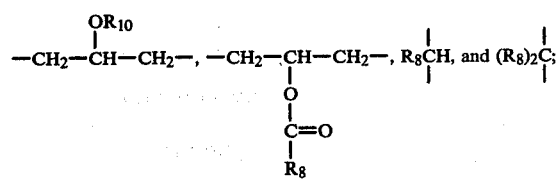

and

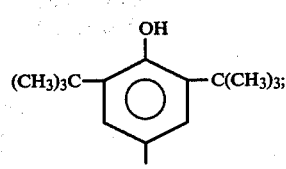

and, when $R_3$ is H or O, when n is 1, and M is selected from the group consisting of:

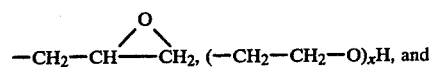

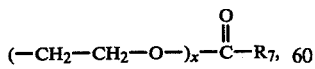

where x is above 1 and up to about 20; and:

when $R_3$ is alkyl of 1 to 6 carbons, hydroxyalkyl having 2 to 3 carbons, or hydroxyalkyl having 2 to 3 carbons wherein the following substituent(s) may be on the carbon beta to N:

an oxirane group that includes the beta carbon and replaces the hydroxyl group;

alkyl of up to 4 carbons, where the hydroxyl group remains on the beta carbon, or is replaced by

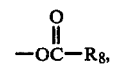

and
an ester group,

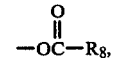

replacing the hydroxyl group, where $R_8$ is selected from the group consisting of an alkyl group, an alkyl alkoxycarbonyl group of an aliphatic monobasic or dibasic acid having from 2 to 20 carbons, and the group:

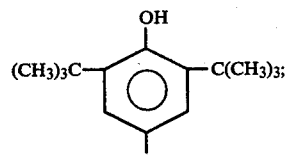

then M is:

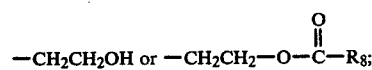

and:
when $R_3$ is hydroxyalkyl and n is 1, M may be H;
and:
$R_3$ may also be

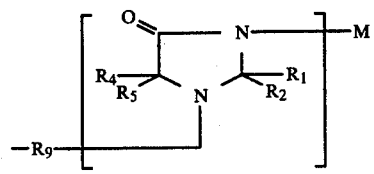

where $R_9$ may be: alkylene of up to 20 carbons, or the residue of a lower alkyl diester of a dibasic acid of 2–20 carbons.

A preferred group of compounds of the invention are depicted by the structure:

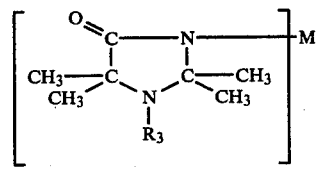

where $R_3$ is lower alkyl, preferably $CH_3$, and when n is 1, M is

where x is above 1 and up to 10; and when n is 2, M is

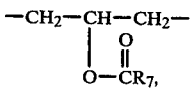

R$_7$ being as defined above.

The most preferred compounds of the invention, that are useful light stabilizers, are described in some of the specific examples that follow. Some examples also demonstrate the preparation and properties of other compounds that, while not within the scope of the structural formula above, are prepared by processes that are within the scope of the invention.

The invention is also concerned with stabilized synthetic polymers and processes for preparing them.

DETAILED DESCRIPTION OF THE INVENTION

The compounds of this invention are stabilizers of organic host materials that are normally subject to thermal, oxidative or actinic light deterioration. Materials which are thus stabilized include synthetic organic polymeric substances including homopolymers, copolymers, and mixtures thereof.

The compounds of this invention are particularly useful as UV light stabilizers, especially for the protection of polyolefins, for instance, polyethylene, polypropylene, poly(butene-1), poly(pentene-1), poly(3-methylbutene-1), poly(4-methylpentene-1), ethylene-propylene copolymers, and the like.

In general, the stabilizers of this invention are employed from about 0.01% to about 5% by weight of the stabilized composition, although this will vary with the particular host polymeric substrate and application. An advantageous range is from about 0.05% to about 2% and especially about 0.1% to about 1%.

For addition to polymeric substrates, the stabilizers can be blended before polymerization or after polymerization during the usual processing operations, for example, by hot-milling, the composition then being extruded, pressed, blow molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, fabrics, filaments or the like to provide effective stabilization. Where the polymer is prepared from a liquid monomer as in the case of styrene, the stabilizer may be dispersed or dissolved in the monomer prior to polymerization or curing.

These compounds can also be used in combination with other additives such as antioxidants, fillers such as glass or other fibers, carbon black, accelerators and the other chemicals used in rubber compounding, plasticizers, color stabilizers, di- and tri-alkyl phosphites and di- and tri-alkylphenyl phosphites, heat stabilizers, ultraviolet light stabilizers, antiozonants, dyes, pigments, metal chelating agents, dyesites and the like. Often combinations of these, such as combinations of compounds of the invention with the phosphites and/or the ultraviolet light stabilizers will produce results in certain applications superior to those expected by the properties of the individual components.

Although the compounds of this invention may to some degree also be effective as thermal stabilizers, if the processing of the polymer is carried out at high temperatures it is advantageous to incorporate additional antioxidants.

In most applications, it is desirable to incorporate into the resin composition a sufficient amount of at least one thermal antioxidant to protect the host plastic against thermal and oxidative degradation. The amount of antioxidant required will be comparable to that of the actinic stabilizer, namely, from about 0.005% to 5%, and preferably from 0.01% to 2% by weight. Representative of such antioxidants are phosphite esters, such as triphenyl phosphite and dibutyl phosphite, and alkyl arylphosphites such as dibutyl-phenylphosphite, and the like.

The compounds of the invention can also be used in combination with other stabilizers, such as thio esters (distearyl thio dipropionate, dilauryl thio dipropionate), heat stabilizers, ultraviolet light stabilizers, antiozonants, and antioxidants.

Excellent results have been obtained using stabilizing compounds of the invention in combination with a preferred class of thermal antioxidants, the hindered phenols. These compounds have been found to provide excellent thermal stabilization with very little discoloration in the compositions of the invention. Among these phenolic antioxidants are included the following, which are representative and exemplary:

2,6-di-tert-butyl-4-methyl phenol
2,6-di-tert-butyl phenol
2,2'-methylene-bis(6-tert-butyl-4-methyl phenol)
n-octadecyl-3-(3,5-di-tert-butyl-4-hydroxyphenyl)-propionate
1,1,3-tris(3-tert-butyl-6-methyl-4-hydroxyphenyl)butane
pentaerythrityl tetra kis[3-(3,5-di-tert butyl-4-hydroxyphenyl)propionate]
di-n-octadecyl-(3,5-di-tert-butyl-4-hydroxybenzyl)-phosphonate
2,4,6-tris(3,5-di-tert-butyl-4-hydroxybenzyl)mesitylene, and
tris(3,5-di-tert-butyl-4-hydroxybenzyl)isocyanurate.

The above phenolic antioxidants are known and many are commercially available. They may be used in the amount from about 0.025% to 5%, and preferably 0.01% to 2% by weight of the host polymeric material plus stabilizers.

Other suitable hindered phenolic antioxidants are disclosed in U.S. Pat. No. 3,920,661, col. 5, lines 8 through 37, and in U.S. Pat. No. 3,971,757, col. 12, line 34 through col. 14, line 17, which disclosures are incorporated herein by reference. They may be used in the same ranges of amounts.

The compounds as represented by Formula I can also be used in combination with other light stabilizers such as 2(2-hydroxyphenyl)benzotriazoles, 2-hydroxybenzophenones, nickel complexes, and particularly, the benzoates.

This invention also relates to synthetic polymeric compositions of matter which are stabilized against ultraviolet light deterioration, and which comprise a synthetic organic polymer normally subject to ultraviolet deterioration containing from about 0.005% to 5% by weight based on the host polymer of the compounds of Formula I and preferably from about 0.01% to about 2% by weight.

The invention is also concerned with a new synthetic technique for the 3-alkylation of 2,2,5,5-tetra-substituted imidazolidin-4-ones using ethylene carbonate or certain of its derivatives as the alkylating agent. To carry out the reaction, according to one preferred embodiment of the process, the substituted imidazolidin-4-one is reacted with alkali (NaOH) with the removal of water, then molten ethylene carbonate is added. After a suitable period at reflux, water may be added, then after a brief time, removed azeotropically. The reaction can be depicted thus:

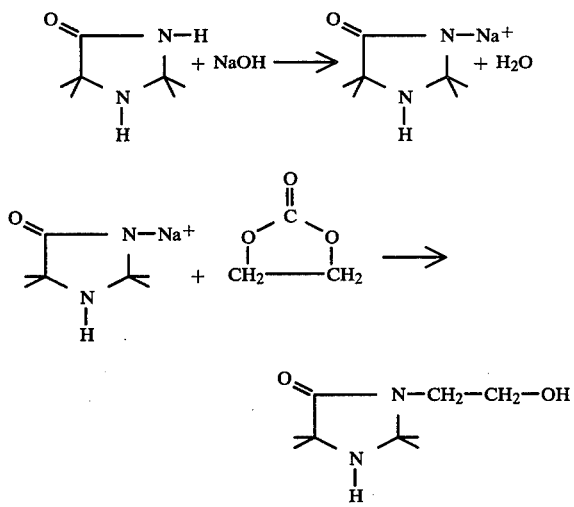

The reaction also goes forward with reactants such as

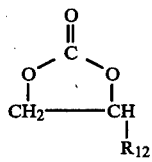

where $R_{12}$ is lower alkyl. In this case the amide nitrogen becomes substituted with a hydroxyethyl group that has a lower alkyl substituent beta to the nitrogen.

In place of a carbonate, the alkali-reacted imidazolidin-4-one can be treated with epichlorohydrin, for alkylation. This reaction results in an additive where n is 2, i.e.:

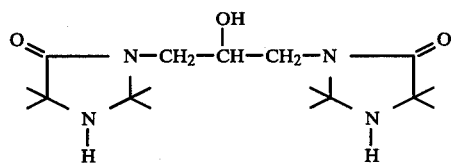

These reaction products are useful stabilizing additives themselves, but in each case, the hydroxyl group, whether terminal or intermediate, can be reacted further, to introduce into the molecule, for example,

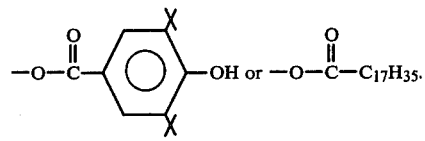

A particular advantage of the use of the stabilizers of the invention is their synergistic action when used in combination with AM-340. Small amounts of each, used in the combination, generally suffice to produce stabilization comparable to that obtained through the use of much larger quantities of either, used alone.

The following examples will illustrate the invention in greater detail. Throughout these examples and elsewhere, parts and percentages are by weight, and temperatures are reported in degrees Celsius, unless stated otherwise.

EXAMPLE 1

Preparation of 1-(βhydroxyethyl)-2,2,5,5-tetramethylimidazolidin-4-one

Tetramethylimidazolidinone (0.15 moles) was dissolved in 75 ml methanol containing 5 drops of concentrated hydrochloric acid. A cooled pressure vessel was then charged with the methanol solution and 0.225 moles of condensed ethylene oxide. The vessel was maintained at 110° for 18 hours. Evaporation of the organic solution gave a quantitative crude yield of the hydroxyethyl compound. Recrystallization from chloroform/hexane and toluene yielded the purified compound m.p. 103°–107°, whose structure was confirmed by the spectral properties of the material.

The structure of this stabilizing compound may be depicted by the formula:

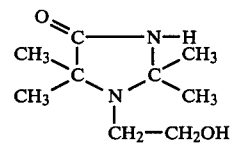

This product, referred to hereafter as Compound 1, has a relatively low molecular weight and is polar in nature. It exhibits stabilizing action but is useful primarily in those host polymeric materials that can accommodate its characteristics.

EXAMPLE 2

Step A

Reaction of Compound 1 with Dimethyl Sebacate

Dimethyl sebacate (0.032 moles) was mixed with 1-(βhydroxyethyl)-2,2,5,5-tetramethylimidazolidin-4-one (0.064 moles) in 100 ml of dried xylene. To the resulting solution was added titanium (IV) isopropoxide (0.917 g). The temperature of the reaction vessel was maintained at 130°–137° while methanol was distilled from the system during a 2½ hour reaction time. After filtration, the organic solution was allowed to cool and the resultant precipitate collected by filtration and washed three times with 75 ml portions of diethyl ether. The crude diester was freed from titanate residues by washing a solution of the material in 200 ml methylene chloride with an equal volume of 2% sodium hydroxide solution. Evaporation of the dried solvent gave a 78% yield of the crude product. Recrystallization from ethanol/water and ethyl acetate provided a material m.p. 172°–176°, identified hereafter as Compound 2.

The structure of this product may be depicted as:

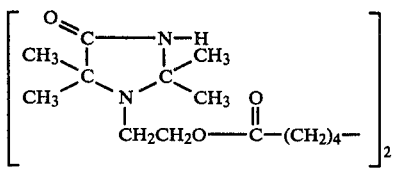

Compound 2, unlike Compound 1, has a relatively high molecular weight and is not very polar in nature. It has stabilizing properties when blended with a compatible host material, as shown in Step B below. Chemically, Compound 2 is Bis β (2,2,5,5-tetramethylimidazolidin-4-one-1-yl)ethyl sebacate.

Step B

Evaluation of Compound 2 as a Light Stabilizer in Polypropylene

Compound 2 was tested in extruded films. Representative samples were dissolved in separate amounts of methylene chloride, respectively, and then several amounts of polypropylene powder (Profax 6501, Hercules) were impregnated, respectively with the solutions, using a Kitchen Aid blender. After the solvent was removed by evaporation under reduced pressure, the polypropylene powder was processed using a compounding extruder equipped with a pelletizer. The pellets were then extruded into film, which was then oriented and slit. Oriented films were drawn from polypropylene pellets at 200° C. Samples were placed on frames and exposed in a Xenon Weather-Ometer (Atlas) until they failed. Failure for these 1-2 mil films was taken as the point at which the tensile strength had been reduced to 50% of its original value as determined by an Instron apparatus. A blank sample containing no ultraviolet light stabilizer was run as a control.

Compound 2 was employed at 0.50% concentration using 0.1% Goodrite 3114 (B. F. Goodrich Co.) antioxidant and 0.05% calcium stearate as heat stabilizers.

TABLE I

| Stability Testing in Polypropylene Film | |
|---|---|
| Compound | Weather-Ometer Lifetime |
| control | ~440 hours |
| 0.5% Compound 2 | 780 hours |

EXAMPLE 3

Preparation of 3-hydroxyethyl-1,2,2,5,5-pentamethylimidazolidin-4-one

A. Preparation of the Reactant, 1,2,2,5,5-Pentamethylimidazolidin-4-one

A 500 ml. resin kettle, equipped with a mechanical stirrer, reflux condenser, thermometer in thermowell, and an addition funnel, was charged with 122.9 g. (0.8642 moles) of 2,2,5,5-tetramethylimidazolidin-4-one, 74.8 g. (0.8642 moles) of 37% formalin solution, and 200 ml. of water. This mixture was stirred without heating as 44.2 g. (0.8642 moles) of 90% formic acid was added over the course of 20 minutes, with the mixture warming up to 30° C. and becoming a solution in this time.

The solution was heated to reflux over a period of 2.5 hours and held at reflux with stirring for an additional 2.5 hours. Cooling to room temperature was followed by filtration to give 98.7 g. of white crystals. The aqueous filtrates were made strongly basic and extracted on a continuous liquid-liquid extractor with methylene chloride for several days. In evaporating off the methylene chloride, a second crop of crystals were produced. In this manner a total of 132.0 g. of white crystals, m.p.: 182°-184° C. was obtained. This material was used in the following synthesis.

B. Reaction of 1,2,2,5,5-Pentamethylimidazolidin-4-one with Ethylene Oxide

A solution of sodium ethoxide was prepared by dissolving 0.5 g sodium in 220 ml absolute ethanol. This solution was transferred to a 12 oz. vessel and mixed with 23.4 g of 1,2,2,5,5-pentamethylimidazolidin-4-one. The vessel was then stoppered and chilled in an ice bath. Then 13.1 g of chilled ethylene oxide was added and the vessel capped. It was then maintained at 110° for 18 hours in a stirred oil bath. The solvent was then evaporated under reduced pressure to give 35.2 g of oily solid. Unreacted pentamethylimidazolidone was removed by recrystallizing the reaction mixture from acetone and petroleum ether. Concentration of the solvent liquors and stripping at 180°/1.0 mm gave the desired product as a residue oil identified by its spectral properties.

This product, hereafter referred to as Compound 3, may be represented by the formula:

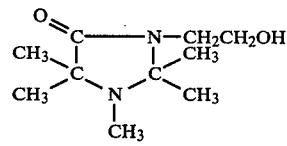

Compound 3 is a good light stabilizer for compatible polymeric host materials, but like Compound 1, it has a relatively low molecular weight and is polar.

EXAMPLE 4

Preparation of 1,2,2,5,5-Pentamethylimidazolidin-4-one-3-yl Ethyl Stearate

A sample of Compound 3, the 3-hydroxyethyl-1,2,2,5,5-pentamethylimidazolidin-4-one (6.4 g) product of Example 3, assayed as 85% pure, was dissolved in 60 ml of dried xylene. To the solution was added 8 g of methyl stearate and 0.9 ml of 25% sodium methoxide solution in methanol, as a catalyst. The solution was then heated for 6 hours at 135°-143° while methanol was removed from the reaction vessel using a short distillation column.

The cooled reaction product was then precipitated with petroleum ether to give a crude product collected by filtration. This was dissolved in 200 ml of methylene chloride, washed twice with equal volumes of water, and filtered. Evaporation of the solvent under reduced pressure gave the stearate ester, m.p. 55°-58°, hereafter referred to as Compound 4.

Compound 4 may be depicted by the formula:

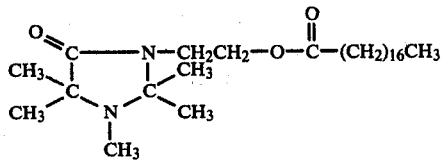

This product was compounded and tested using the procedure described in Example 2. Compound 4 was compared to several commercial light stabilizers, namely, Tinuvin 770, Tinuvin 622, and Tinuvin 144, which are products of Ciba Geigy Corp. Also tested were CH944 (Chimosa S.p.A.), and AM340 (Ferro Corp.).

The results are reported below in Table II.

TABLE II

Comparative Stability Testing of Compound 4 in Polypropylene Film

| Test | | Weather-Ometer Lifetime, Hrs. |
|---|---|---|
| 1. | 0.25 CH944 | 1970 |
| 2. | 0.25 Tinuvin 622 | 1750 |
| 3. | 0.25 pentamethyl stearate derivative of Example 4; Compound 4 | 1955 |
| 4. | 0.25 AM340 | 1350 |
| 5. | 0.25 AM340 + 0.25 pentamethyl stearate derivative of Example 4; Compound 4 | 2550 |
| 6. | Tinuvin 144 | 1110 |
| 7. | Tinuvin 770 | 2460 |

CH944 (Chimasorb 944) is a commercially available stabilizer sold by Chimosa Chimica Organica SpA of Bologna, Italy.
Tinuvin 622: poly(1-β-hydroxyethyl-2,2,6,6-tetramethyl piperidin-4-ol) succinate.
AM 340: 3',4'-di-t-butyl phenyl-3,5-di-t-butyl-4-hydroxy benzoate.
Tinuvin 144: di(1', 2', 2', 6', 6'-pentamethyl-piperidin-4'-ol)2-n-butyl-2-(3'',5''-di-t-butyl-4''-hydroxy benzyl) malonate.
Tinuvin 770: di(2,2,6,6-tetramethyl piperidin-4-ol) sebacate.

The pronounced mutual enhancement (synergism) between Compound 4 and AM340 is shown in Tests 3, 4 and 5 in Table II above. This behavior is typical of the imidazolidinone compounds of this invention.

EXAMPLE 5

Preparation of 3-polyethoxylated-2,2,5,5-tetramethylimidazolidin-4-one

A solution of 2,2,5,5-tetramethylimidazolidone in t-butyl alcohol was prepared by stirring and warming 14.3 g of the compound with 150 ml of t-butyl alcohol which had been distilled from sodium. After the addition of 2.24 g of potassium t-butoxide as a basic catalyst, 8.8 g of ethylene oxide was bubbled into the reaction over a 40 minute period at 28°–32°. The solution was then heated under a dry ice condenser at 40°–50° for 1½ hours and 50° for 3½ hours. The reaction mixture was shown to contain unreacted imidazolidinone by thin layer chromatography (TLC).

An additional 8.8 g of ethylene oxide was then added over a 45 minute period at 20°–26° followed by heating at 50° for 1½ hours. The solvent was then evaporated and the material stripped under reduced pressure at 160°/1.1 mm to give the product as a thick liquid, with a hydroxyl number of 235.6 mg KOH/g.

This product, referred to hereafter as Compound 5, may be represented by the formula:

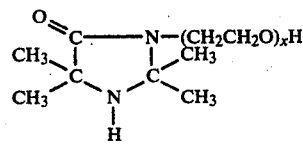

where x has a value of about 3. It is a useful light stabilizer for polyolefins.

EXAMPLE 6

Preparation of 3-polyethoxylated-2,2,5,5-tetramethylimidazolidin-4-one stearate

The polyethoxylated product of Example 5, Compound 5, 12.5 g, was weighed into a small flask and 12.5 g methyl stearate added. To this mixture was added 1.35 g of 25% sodium methoxide solution in methanol as a transesterification catalyst, and 40 ml of azeotropically dried xylene as a solvent.

The reaction mixture was heated for 2 hours at 135°–143°, while 2.7 ml of distillate was collected at 59°–63°. The hot solution was cooled and diluted with petroleum ether to a total volume of 300 ml. The crude product was then collected by filtration. It was dissolved in 220 ml of methylene chloride, and insoluble material was removed by filtration. After being washed with water, the solution was dried and evaporated to yield a product in the form of a waxy solid, identified by its spectral properties.

This material, referred to hereafter as Compound 6, may be represented by the formula:

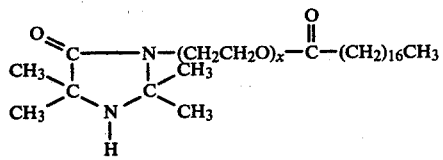

where x, as above, is about 3.

Evaluations

The products of Examples 5 and 6, i.e. Compounds 5 and 6, were evaluated, using the procedure of Example 2, Step B, and their performance was compared with that of a commercial stabilizer. The results are presented below in Table III.

TABLE III

Comparative Stability Testing of Compounds 5 and 6 in Polypropylene Films

| Compound | Weather-Ometer Lifetime, Hrs. |
|---|---|
| blank | 400 |
| 0.25% Product of Ex. 5 | 495 |
| 0.25% Product of Ex. 6 | 1340 |
| 0.25% Tinuvin 622 | 1120 |

EXAMPLE 7

Preparation of 3-polyethoxylated-2,2,5,5-tetramethylimidazolidin-4-one 3,5-di-t-butyl-4-hydroxybenzoate The polyethoxylated product of Example 5, Compound 5, 7.5 g, was weighed out and mixed with 7.5 g of methyl 3,5-di-t-butyl-4-hydroxybenzoate in 40 ml of azeotropically dried xylene. Then 0.92 g of 25% sodium methoxide solution in methanol was added to the reaction mixture. The reaction mixture was heated for 29 hours at 138°–140° while product methanol was distilled from the reaction vessel over a short column. The xylene was then removed from the solution at 100° under reduced pressure. The residue was taken up in 200 ml of methylene chloride, and the organic solution was then washed with water. After drying, evaporation of the methylene chloride yielded a thick oily product. It was freed of unreacted methyl 3,5-di-t-butyl-4-hydroxybenzoate by stripping at 180°/0.2 mm. The product was obtained as a thick brown oil identified by its spectral properties.

This product, referred to hereafter as Compound 7, may be represented by the formula:

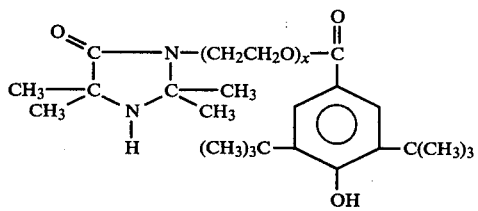

where x, as above, is about 3. It has excellent stabilizing properties.

EXAMPLE 8

3-Hydroxyethyl-1,2,2,5,5-Pentamethylimidazolidin-4-one Stearate

The procedure followed in Example 7 was followed generally. However, the initial reactant compounds were Compound 3 and methyl stearate. The final product was 3-hydroxyethyl-1,2,2,5,5-pentamethylimidazolidin-4-one stearate, referred to hereafter as Compound 8. It has excellent stabilizing properties.

Compounds 7 and 8 were evaluated, using the procedure of Example 2, Step B, and their performances were compared to that of a commercial stabilizer. The results are presented below in Table IV.

TABLE IV

Comparative Stability Testing of Compounds 7 and 8 in Polypropylene Films

| Compound | Weather-Ometer Lifetime, Hrs. |
| --- | --- |
| blank | 400 |
| 0.25% Compound 7 | 1340 |
| 0.25% Compound 8 | 2010 |
| 0.25% Tinuvin 622 | 1120 |

EXAMPLE 9

Preparation of 3-Hydroxyethyl-2,2,5,5-tetramethylimidazolidin-4-one using Ethylene Carbonate Alkylation A 2 liter 3-necked flask was equipped with mechanical stirrer, Dean Stark trap and dropping funnel and charged with 106.7 g. of 2,2,5,5-tetramethyl-imidazolidin-4-one (0.75 moles) and 1 liter of azeo dried xylene. After the solution had been brought to reflux, 63 g. of a 50% aqueous sodium hydroxide solition was gradually added and water removed from the system. After about 2 hours, 44 ml. of water (96.5% theoretical water and water of reaction) were collected.

The reaction mixture was then cooled and 67.5 g. of molten ethylene carbonate added. Reflux was then continued for 24 hours. The reaction mixture was cooled again and 50 ml water was added, after which the mixture was heated under gentle reflux for 3 hours.

The organic solution was then dried by azeotropic distillation, cooled, and the inorganic solids removed by filtration. Evaporation of the organic solvent yielded the product as a thick liquid, weight 122.2 g. It was purified by distillation at 116°–118°/0.1–0.13 mm. to give a white solid which was purified by recrystallization from heptane. The pure compound melted at 58°–60°. Its structure was determined by its spectral properties. It is referred to hereafter as Compound 9.

EXAMPLE 10

Preparation of 2,2,5,5-tetramethylimidazolidin-4-one-3-yl Ethyl 3,5-di-t-butyl-4-hydroxybenzoate A 100 ml. 3-necked reaction flask was charged with 9.0 g. of 3-hydroxyethyl-2,2,5,5-tetramethylimidazolidin-4-one (0.048 moles) and 12.7 g. of methyl 3,5-di-t-butyl-4-hydroxybenzoate (0.048 moles). The flask was fitted with a magnetic stirrer, thermometer and short distillation column. Azeotropically dried xylene (35 ml.) was added together with 1.64 ml. of a 25% solution of sodium methoxide in methanol.

The vessel was heated slowly to 140°–142° with distillation of mixed methanol/xylene at 45°–88°. After about 2 hours' heating nearly the theoretical amount of methanol had been isolated. Heating was continued for a total of 14 hours when 15 ml. of xylene was distilled from the system. The rest of the solvent was removed at 100° under reduced pressure to give a thick green oil which was dissolved in 200 ml. methylene chloride to form a dark solution.

The solution was washed 3 times with 200 ml. portions of water and dried with anhydrous sodium sulfate. The organic solution was filtered through filter aid when a color change from green to orange occurred. Evaporation of the solvent yielded 17.8 g. of a tan solid m.p. 117°–126°. After two recrystallizations from chloroform/hexane the pure compound m.p. 133°–135° was obtained. Its structure was confirmed by spectral analysis. The compound, referred to hereafter as Compound 10, may be represented by the formula:

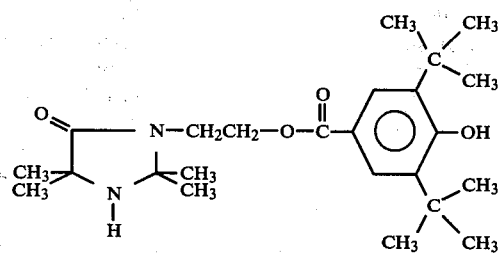

Evaluations

Compound 10 was evaluated, using the procedure of Example 2, Step B, and its performance compared to previous compounds and a commercial stabilizer. The results are presented below in Table V.

TABLE V

Comparative Stability Testing of
Compound 10 in Polypropylene Films

| Compound | Weather-Ometer Lifetime, Hrs. |
| --- | --- |
| blank | 500 |
| 0.25% Product of Example 10 | 2410 |
| 0.25% Tinuvin 622 | 2500 |
| 0.25% Product of Example 5 | 1950 |
| 0.25% Product of Example 7 | 1970 |
| 0.25% Product of Example 8 | 1980 |

EXAMPLE 11

Preparation of
1,3-Bis-(2,2,5,5-Tetramethylimidazolidinone-3-yl)-2-Propanol

A 500 ml. resin kettle, equipped with mechanical stirrer, thermometer in thermowell, addition funnel, and Dean-Stark water trap fitted with a reflux condenser, was charged with 136.7 g. (0.8753 moles) of 1,2,2,5,5-pentamethylimidazolidin-4-one and 200 ml. of reagent grade xylene. This was heated with stirring to reflux. At this point 70.0 g. of 50% sodium hydroxide solution (0.8753 moles) was very gradually added over the course of one and one quarter hours. The reactor contents were stirred at reflux for an additional half hour, with a total collection of 51–52 ml. of water phase.

The reaction solution was then cooled to room temperature, at which point a solution of 40.6 g. of 99.6% epichlorohydrin and 25 ml. of dimethyl formamide was added with stirring dropwise over the course of one hour; cooling was necessary to prevent the exotherm from exceeding 115° C. Cooling was continued after the addition was over to return the reactor contents to room temperature; stirring was then continued for some time.

The reactor contents were reheated to reflux over the course of several hours to complete the reaction, then allowed to cool to room temperature. The reactor contents were placed in a stirring mixing tank and 600 ml. of water was added. The phases were separated and the xylene phase was extracted several times with water. The combined water phases were then continuously extracted with methylene chloride, for several days. Evaporation of the solvent gave a crude solid that was recrystallized from toluene. The original xylene phases were dried over anhydrous sodium sulfate and distilled at atmospheric pressure to recover the solvent. The residue crystallized on cooling. Recrystallization of this material also gave good product. In this manner a total of 62.4 g. of recrystallized material, m.p.: 172°–175° C. was obtained. This material was used for the syntheses described in the following examples.

EXAMPLE 12

Preparation of
1,3-Bis-(1,2,2,5,5-Pentamethylimidazolidinone-3-yl)-2-propyl 3,5-Di-t-Butyl-4-Hydroxybenzoates Part I. Preparation of the Acid Chloride A 500 ml. resin kettle, equipped with mechanical stirrer, thermometer in thermowell, addition funnel, and Dean-Stark trap fitted with a reflux condenser, was charged with 12.4 g. (0.0487 moles) of 98% 3,5-di-t-butyl-4-hydroxybenzoic acid and 200 ml. of xylenes. The mixture was heated with stirring to about 70° C., at which point 7.2 g. (0.0487 moles + 25% excess) of 97% thionyl chloride was added over the course of ten minutes. The yellow solution was then heated to reflux and held at reflux as a total of 100 ml. of overheads was distilled off. This contained the unreacted excess thionyl chloride and xylenes. Upon cooling to room temperature, the reaction mixture was filtered to remove a small amount (less than 1.0 g.) of insoluble material. The filtrates were used in the following Part II.

Part II. Reaction of the Acid Chloride with the Product of Ex. 11

A 500 ml. resin kettle, equipped with mechanical stirrer, thermometer in thermowell, addition funnel, and Dean-Stark trap fitted with a reflux condenser, was charged with 23.5 g. of the recrystallized product material of Example 11 and 200 ml. of xylene. This mixture was heated to 95° C., at which point the above, clear red-brown xylene solution of the acid chloride was added to the clear, yellow solution in the pot, dropwise, over the course of two hours and 15 minutes. The reaction mixture was heated and stirred at reflux for several hours, during which time approximately 220 ml. of overheads were collected (discarded).

The mixture was cooled to room temperature, then a saturated aqueous solution of sodium bicarbonate, containing 10.0 g. (0.12 moles) of sodium bicarbonate, was added over the course of one hour and one-half, followed by an additional hour of stirring.

The phases were separated; the xylene phase was distilled under atmospheric pressure to recover the xylene. The residue, a brown glass, was vacuum dried at 100° C., to give a crude material of 31.0 g. weight. Recrystallization afforded 21.5 g. of crystalline material, m.p.: 133°–135° C. A second recrystallization of this material gave 13.7 g. of fine crystals, m.p.: 150°–152° C. The structure was confirmed by the spectrophotometric analyses, to conform to that of 1,3-Bis-(1,2,2,5,5-Pentamethylimidazolidinone-3-yl)-2-propyl 3,5-di-ti-butyl-4-hydroxybenzoate; hereafter, Compound 12.

EXAMPLE 13

Preparation of
1,3-Bis-(1,2,2,5,5-Pentamethylimidazolidinone-3-yl)-2-Propyl Stearate A 500 ml. resin kettle, equipped with mechanical stirrer, reflux condenser, thermometer in thermowell, and addition funnel, was charged with a mixture of 26.5 g. of the product of Example 11 and 200 ml. xylene. This mixture was heated with stirring to reflux, then 14.8 g. of stearoyl chloride in 50 ml. xylene was added over the course of one hour and 20 minutes. The resulting mixture was heated at reflux for several hours, then cooled to room temperature, at which time a saturated aqueous solution containing 10.0 g. of sodium bicarbonate (0.12 moles) was added with stirring.

The phases were then separated. The xylene phase was evaporated to dryness on a rotary evaporator under reduced pressure. The clear, brown oil was taken up in heptane and chilled in a freezer. In this manner a total of 28.2 g. of crude product was obtained. This material was dissolved in hot heptane, treated with decolorizing carbon, and crystallized as described above. This second recrystallization and purification gave 19.0 g. of crystals, m.p.: 52°–54° C.; the results of the spectral analyses were consistent with the structure associated with the name, 1,3-Bis-(1,2,2,5,5-pentamethylimidazolidinone-3-yl)-2-propyl stearate, hereafter, Compound 13.

Evaluations

Compounds 12 and 13 were evaluated using the procedure of Example 2, Step B, and then performances were compared to that of a commercial stabilizer. The results are presented below in Table VI.

TABLE VI
Comparative Stability Testing of Compounds 12 and 13 in Polypropylene Films

| Compound | Weather-Ometer Lifetime, Hrs. |
| --- | --- |
| 0.25% Product of Example 12 | 1330 |
| 0.5% Product of Example 12 | 1630 |
| 0.25% Product of Example 12 + 0.25% AM 340 | 1720 |
| 0.25% Product of Example 13 | 1850 |
| 0.5% Product of Example 13 | 1780 |
| 0.25% Product of Example 13 + 0.25% AM 340 | 1870 |
| 0.25% Tinuvin 770 | 1620 |
| 0.25% Tinuvin 622 | 1460 |

General

In the polyoxyethylated compounds of the invention, the value of x preferably is from above 1 (x is a statistical average value) to about 10, and more preferably, is about 3.

Examples of other specific compounds of the invention, that exhibit light stabilizing properties, and that conform to Formula 1, are as follows:

14.
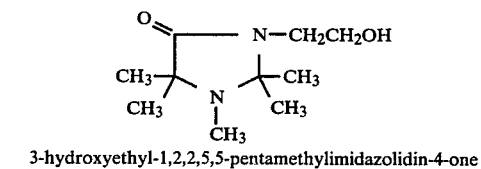
3-hydroxyethyl-1,2,2,5,5-pentamethylimidazolidin-4-one

15.
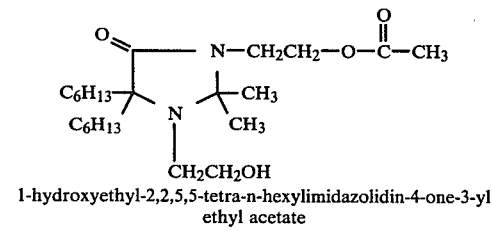
1-hydroxyethyl-2,2,5,5-tetra-n-hexylimidazolidin-4-one-3-yl ethyl acetate 16.
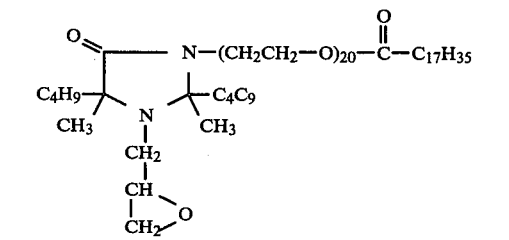
3-vigintiethoxy-1-(2,3-epoxypropyl)2,5-dimethyl-2,5-di-n-butyl-imidazolidin-4-one stearate 17.
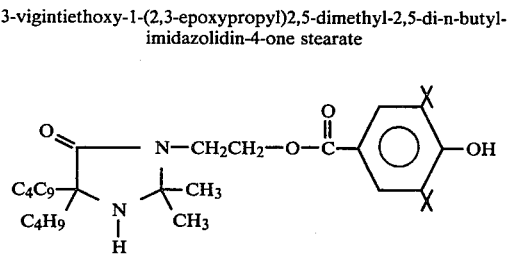
2,2-dimethyl-5,5-dibutylimidazolidin-4-one-3-yl ethyl 3,5-di-t-butyl-4-hydroxybenzoate 18.
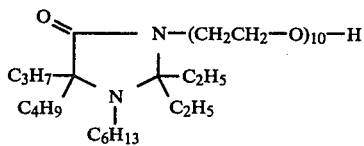
3-decaethoxy-1-n-hexyl-2,2-diethyl-5-butyl-5-propylimidazolidin-4-one 19.
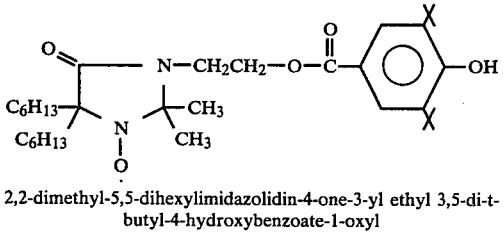
2,2-dimethyl-5,5-dihexylimidazolidin-4-one-3-yl ethyl 3,5-di-t-butyl-4-hydroxybenzoate-1-oxyl 20.
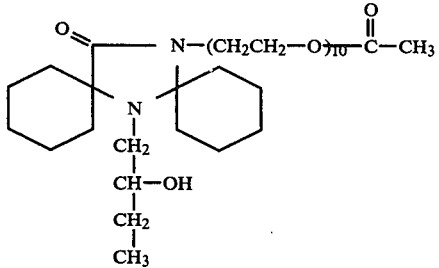
7-(1-2-hydroxy-n-butyl)-14-decaethoxyacetyl-7,14-diaza-15-oxo-dispiro[5.1.5.2] pentadecane 21.
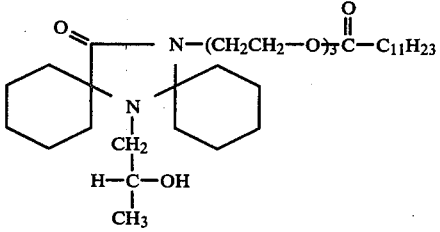
6-(2-hydroxypropyl)-13-triethoxylauroyl-6,13-diaza-14-oxo-dispiro[4.1.5.2]tetradecane 22.
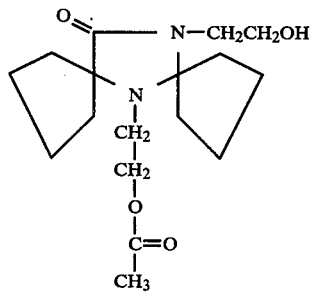
6-(2-acetoxyethyl)-12-hydroxyethyl-6,12-diaza-13-oxa-dispiro[4.1.4.2]tridecane 23.
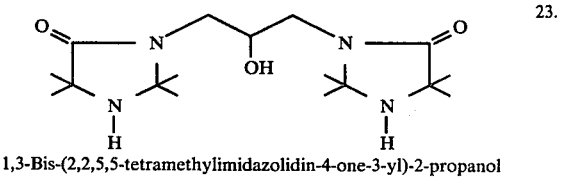
1,3-Bis-(2,2,5,5-tetramethylimidazolidin-4-one-3-yl)-2-propanol -continued

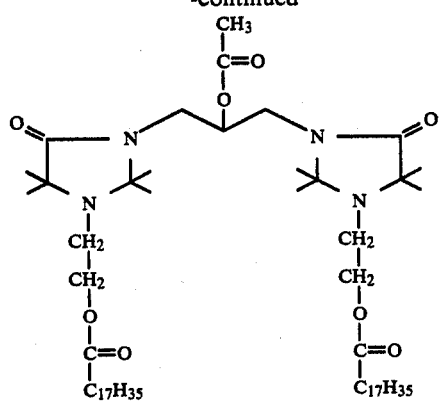
1,3-Bis-(1,2-stearoyloxyethyl-2,2,5,5-tetramethylimidazolidin-4-one-3-yl)-2-propyl acetate

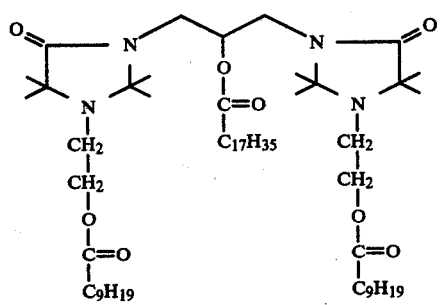
1,3-Bis-(1-2-decanoyloxyethyl-2,2,5,5-tetramethylimidazolidin-4-one-3-yl)-2-propyl stearate

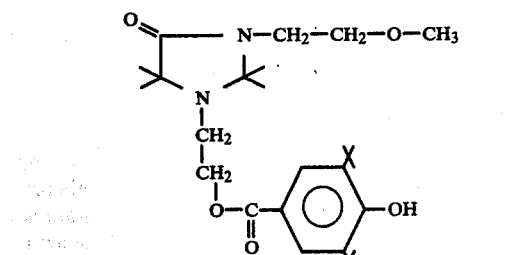
1-[2-(3,5-di-t-butyl-4-hydroxybenzoyloxy)ethyl)]-2,2,5,5-tetramethyl-3-methoxyethyl-imidazolidin-4-one

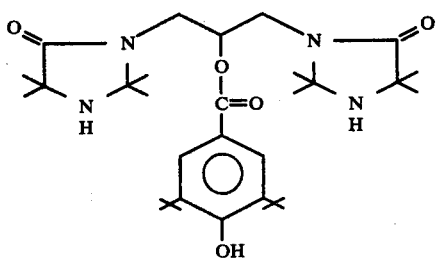
1,3-Bis-(2,2,5,5-tetramethylimidazolidin-4-one-3-yl)-2-propyl 3,5-di-t-butyl-4-hydroxybenzoate

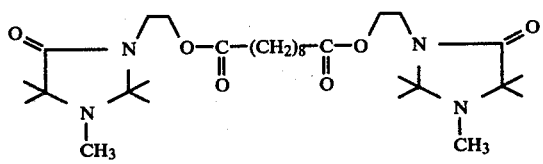
Bis (1,2,2,5,5-pentamethylimidazolidin-4-one-3-yl)-ethyl sebacate

-continued

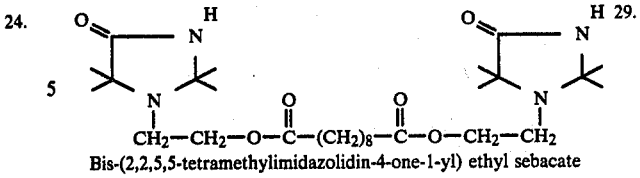
Bis-(2,2,5,5-tetramethylimidazolidin-4-one-1-yl) ethyl sebacate

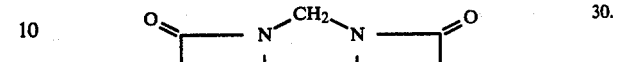
Bis-(1,2,2,5,5-pentamethylimidazolidin-4-one-3-yl) methane

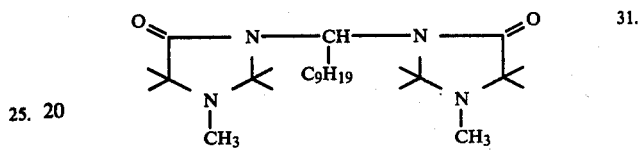
Bis(1,2,2,5,5-pentamethylimidazolidin-4-one-3-yl)-1,1-decane

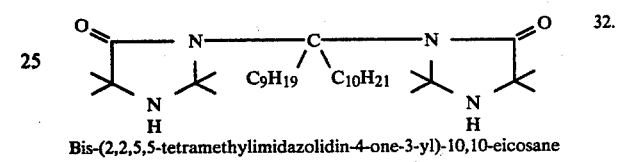
Bis-(2,2,5,5-tetramethylimidazolidin-4-one-3-yl)-10,10-eicosane

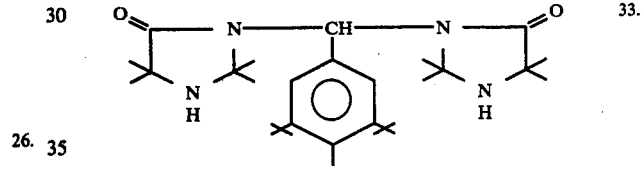
Bis-(2,2,5,5-tetramethylimidazolidion-4-one-3-yl)-α-3,5-di-t-butyl-4-hydroxytoluene

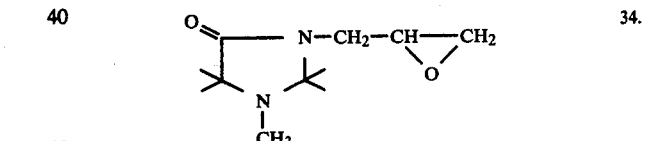
3-(2,3-epoxypropyl)-1,2,2,5,5-pentamethylimidazolidin-4-one

All of these specific compounds exhibit light stabilizing properties in compatible host polymeric materials.

Polymers of which the light aging can be delayed or prevented by the compounds of the Formula I according to the invention, for example, the following categories of industrially important polymeric and copolymeric materials.

1. Polymers which are derived from singly or doubly unsaturated hydrocarbons, for example, polyolefins such as polyethylene, which may be cross-linked, polypropylene, polybutene-1, polyisobutene, polymethylbutene-1, polymethylpentene-1, polyisoprene, polybutadiene, polystyrene, copolymers of the monomers on which these homopolymers mentioned are based, such as ethylene-propylene copolymers, propylene-butene-1 copolymers, propylene-isobutene copolymers, styrene-butadiene copolymers, and terpolymers of ethylene and propylene with a diene such as, for example, hexadiene, dicyclopentadiene or ethylidenenorbornene; mixtures of the above-mentioned homopolymers such as, for example, mixtures of polypropylene and polyethylene, polypropylene and polybutene-1, or polypropylene and polyisobutylene, or of butadiene-acrylonitrile copolymer with a styrene-butadiene copolymer.

2. Vinyl polymers containing halogen, such as polyvinyl chloride, polyvinylidene chloride, polyvinyl fluoride, polychloroprene and chlorinated rubbers.

3. Polymers which are derived from $\alpha,\beta$-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, stearate, benzoate and maleate, polyvinyl butyral, polyallyl phthalate, polyallylmelamine, and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as polyoxymethylenes which contain ethylene oxide as a comonomer.

7. Polyphenylene oxides.

8. Polyurethanes and polyureas.

9. Polycarbonates.

10. Polysulphones.

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and dialcohols and/or from hydroxycarboxylic acids, or the corresponding lactones, such as polyethylene glycol terephthalate, polybutylene terephthalate, poly-1,4-dimethylol-cyclohexane terephthalate, and their starting materials, such as lower terephthalic acid alkyl esters.

13. Cross-linked polymers which are derived from aldehydes, on the one hand, and phenols, ureas and melamines, on the other, such as phenol-formaldehyde, urea-formaldehyde and melamine-formaldehyde resins.

14. Alkyd resins, such as glycerine-phthalic acid resins and their mixtures with melamine-formaldehyde resins.

15. Unsaturated polyester resins which are derived from copolyesters or saturated and unsaturated dicarboxylic acids with polyhydric alcohols, with vinyl compounds as cross-linking agents, and also their halogen-containing modifications of low flammability.

16. Natural polymers, such as cellulose, rubber, proteins, and their chemically modified derivatives, such as cellulose acetates, propionates and butyrates, or the cellulose ethers, such as methylcellulose.

Preferred polymers are polyethylene of high and low density, polypropylene, polybutadiene, polyvinyl chloride, polystyrene and its copolymers, and mixtures thereof.

The new compounds are added to the host polymeric substrates in a concentration of 0.01 to 5% by weight, calculated relative to the material to be stabilized. Preferably, 0.05 to 1.5, and especially preferentially 0.1 to 0.8% by weight of the compounds, calculated relative to the material to be stabilized, are incorporated into the latter.

The incorporation can be effected after the polymerization, for example by mixing the compounds and optionally further additives into the melt in accordance with the industrially customary methods, before or during shaping, or by applying the dissolved or dispersed compounds to the polymer, if necessary with subsequent evaporation of the solvent.

The new compounds can also be added to the polymers to be stabilized in the form of a master batch which contains these compounds, for example, in a concentration of 2.5 to 25% by weight.

In the case of cross-linked polyethylene, the compounds are added before cross-linking.

As further additives, not already mentioned, that may be used together with the stabilizers according to the invention, to stabilize compatible host polymers, the following are representative.

1. Antioxidants.

1.1 Simple 2,6-dialkylphenols such as, for example, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones such as, for example, 2,5-di-tert.-butyl-hydroquinone, 2,5-di-tert.-butyl-4-hydroxy-anisole, tris-(3,5-di-tert.-butyl-4-hydroxyphenyl)phosphite, 3,5-di-tert.-butyl-4-hydroxyphenylstearate and bis-(3,5-di-tert.-butyl-4-hydroxyphenyl)-adipate.

1.3 Hydroxylated thiodiphenyl ethers such as, for example, 2,2'-thio-bis-(6-tert.-butyl-4-methylphenol), and 4,4'-bis-(2,6-dimethyl-4-hydroxyphenyl)-disulphide.

1.4 Alkylidene-bisphenols such as, for example, 2,2'-methylene-bis-(6-tert.butyl-4-methylphenol), 2,2'-methylene-bis-[4-methyl-6-($\alpha$-methylcyclohexyl)-phenol], and ethylene-glycol-bis-[3,3-bis-(3'-tert.butyl-4'-hydroxyphenyl)butyrate].

1.5 O-, N- and S-benzyl compounds such as, for example, 3,5,3',5'-tetra-tert.butyl-4,4'-dihydroxydibenzyl ether, tri-(3,5-di-tert.butyl-4-hydroxybenzyl)-amine, and bis-(4-tert.butyl-3-hydroxy-2,6-dimethylbenzyl)-dithiol terephthalate.

1.6 Hydroxybenzylated malonic esters such as, for example, 2,2-bis-(3,5-di-tert.butyl-2-hydroxybenzyl)-malonic acid dioctadecyl ester, and 2,2-bis-(3,5-di-tert.butyl-4-hydroxybenzyl)malonic acid di-[4-(1,1,3,3-tetramethylbutyl)-phenyl]-ester.

1.7 Hydroxybenzyl-aromatics such as, for example, 1,3,5-tri-(3,5-di-tert.butyl-4-hydroxybenzyl)-2,4,6-trimethylbenzene and 1,3,5-tris-(3,5-di-tert.butyl-4-hydroxybenzyl)-isocyanurate.

1.8 Amides of $\beta$-(3,5-di-tert.butyl-4-hydroxyphenyl)-propionic acid, such as, for example, 1,3,3-tri-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.

1.9 Esters of $\beta$-(3,5-di-tert.butyl-4-hydroxyphenyl)-propionic acid with monohydric or polyhydric alcohols, such as, for example, methanol, ethanol, octadecanol, 1,6-hexanediol, 1,9-nonanediol, ethylene glycol, tris-hydroxyethyl-isocyanurate, and 4-hydroxymethyl-1-phospha-2,6,7-trioxabicyclo[2,2,2]octane.

1.10 Esters of $\beta$-(5-tert.butyl-4-hydroxy-3-methylphenylpropionic acid with monohydric or polyhydric alcohols such as, for example, methanol, ethanol, octadecanol, 1,6-hexanediol, 1,9-nonanediol, ethylene glycol; and 4-hydroxymethyl-1-phospha-2,6,7-trioxabicyclo[2,2,2]octane.

1.11 Esters of 3,5-di-tert.butyl-4-hydroxyphenylacetic acid with monohydric or polyhydric alcohols.

1.12 Acylaminophenols such as, for example, N-(3,5-di-tert.-butyl-4-hydroxyphenyl)-stearic acid amide and N,N'-di-(3,5-di-tert.butyl-4-hydroxyphenyl)-thiobisacetamide.

1.13 Benzylphosphonates such as, for example, 3,5-di-tert.butyl-4-hydroxybenzyl-phosphonic acid dimethyl ester.

1.14 Aminoaryl derivatives, such as, for example, phenyl-1-naphthylamine.

2. UV absorbers and light protection agents:

2.1 2-(2'-Hydroxyphenyl)-benztriazoles, such as, for example, the 5'-methyl-, 3'5'-di-tert.butyl-, 5'-tert.butyl-3'-methyl-5'-carbomethoxyethyl-, and 5-chloro-3',5'-di-tert.-amyl-derivative.

2.2 2,4-Bis-(2'-hydroxyphenyl)-6-alkyl-s-triazines, such as, for example, the 6-ethyl-, 6-heptadecyl or 6-undecyl-derivative.

2.3 2-Hydroxy-benzophenones, such as, for example, the 4-hydroxy-, 4-methoxy-, 4-octoxy, 4-decyloxy-, 4-dodecyloxy-, 4-benzyloxy, 4,2',4'-trihydroxy- or 2'-hydroxy-4,4'-dimethoxy-derivative.

2.4 1,3-Bis-(2'-hydroxy-benzoyl)-benzenes, such as, for example, 1,3-bis-(2'hydroxy-4'-hexyloxy-benzoyl)-benzene.

2.5 Esters of optionally substituted benzoic acids such as, for example, phenyl salicylate, and 3,5-di-tert.butyl-4-hydroxybenzoic acid 2,4-di-tert.butyl-phenyl ester, octadecyl ester or 2-methyl-4,6-di-tert.butyl-phenyl ester.

2.6 Acrylates, such as, for example, α-cyano-β,β-diphenylacrylic acid ethyl ester or isooctyl ester.

2.7 Nickel compounds, such as, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyldiethanolamine; nickel complexes of bis[2-hydroxy-4-(1,1,3,3-tetramethylbutyl)-phenyl]-sulphone, such as the 2:1 complex, optionally with additional ligands such as 2-ethyl-caproic acid, and nickel dibutyldithiocarbamate.

2.8 Sterically hindered amines, such as, for example, 4-benzoyloxy-2,2,6,6-tetramethylpiperidine, and 4-stearoyloxy-2,2,6,6-tetramethylpiperidine.

2.9 Oxalic acid diamides, such as, for example, 4,4'-di-octyloxy-oxanilide.

3. Metal deactivators, such as, for example, oxanilide, isophthalic acid dihydrazide, sebacic acid bis-phenylhydrazide, and N,N'-bis-(3,5-di-tert.butyl-4-hydroxyphenylpropionyl)hydrazine.

4. Phosphites, such as, for example, triphenylphosphite, diphenylalkylphosphites, phenyldialkylphosphites, tri-(nonylphenyl)-phosphite, trilaurylphosphite, and tri-(4-hydroxy-3,5-di-tert.butylphenyl)-phosphite.

5. Compounds which destroy peroxides, such as, for example, esters of β-thiodipropionic acid.

6. Polyamide stabilizers, such as, for example, copper salts in combination with iodides and/or phosphorus compounds and salts of divalent manganese.

7. Basic co-stabilizers, such as, for example, melamine, benzoguanamine, polyvinylpyrrolidone, dicyanadiamide, triallylcyanurate, urea derivatives, alkali metal salts and alkaline earth metal salts of higher fatty acids, for example Ca stearate.

8. PVC stabilizers, such as, for example, organic tin compounds.

9. Nucleating agents, such as for example 4-tert.butyl-benzoic acid, adipic acid and diphenylacetic acid.

10. Other additives, such as, for example, plasticizers, lubricants, emulsifiers, fillers, carbon black, asbestos, kaolin, talc, glass fibres, pigments, optical brighteners, flameproofing agents and antistatic agents.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

What is claimed is:

1. A process for hydroxyalkylating a 2,2,5,5-tetra(-lower alkyl) imidazolidin-4-one comprising
   (a) reacting it with an aqueous sodium hydroxide solution,
   (b) removing water present and water formed by the reaction, then
   (c) bringing the reaction product into contact with molten ethylene carbonate, then
   (d) adding water and heating at reflux, then
   (e) drying and recovering the hydroxy alkylated product.

2. The process of claim 1 wherein the initial reactant is 2,2,5,5-tetramethylimidazolidin-4-one and the product of step (e) is 3-hydroxyethyl-2,2,5,5-tetramethylimidazolidin-4-one.

* * * * *